| United States Patent [19] | [11] Patent Number: 4,936,074 |
| Graham | [45] Date of Patent: Jun. 26, 1990 |

[54] PROCESS FOR PREPARING SOLID ENCAPSULATED MEDICAMENT

[75] Inventor: Dean M. Graham, Hobart, N.Y.

[73] Assignee: D. M. Graham Laboratories, Inc., Hobart, N.Y.

[21] Appl. No.: 272,734

[22] Filed: Nov. 17, 1988

[51] Int. Cl.⁵ .......................... A61K 9/64; B65B 7/28; B65B 63/08

[52] U.S. Cl. ....................................... 53/440; 53/471; 53/900; 424/454

[58] Field of Search ................. 53/400, 440, 467, 471, 53/474, 477, 478, 900; 424/451, 454, 456; 426/138

[56] References Cited

U.S. PATENT DOCUMENTS

| 3,432,592 | 3/1969 | Speiser | 264/328.18 |
| 4,028,024 | 6/1977 | Moreland | 53/900 X |
| 4,497,157 | 2/1985 | Dürr et al. | 53/440 X |
| 4,591,475 | 5/1986 | Tomka et al. | 264/328.14 |
| 4,655,840 | 4/1987 | Wittwer et al. | 106/125 X |
| 4,673,438 | 6/1987 | Wittwer et al. | 264/328.18 X |
| 4,734,149 | 3/1988 | Brown | 53/478 X |

FOREIGN PATENT DOCUMENTS

1933562  1/1971  Fed. Rep. of Germany ........ 53/467

*Primary Examiner*—Robert L. Spruill
*Assistant Examiner*—Linda B. Johnson
*Attorney, Agent, or Firm*—Klauber & Jackson

[57] ABSTRACT

The present invention relates to the preparation of encapsulated products containing a solid dosage form prepared with up to 35% of an edible matrix material. The composition may be introduced into the capsule by injection molding or extrusion, and the resulting capsule products exhibit the favorable texture of a capsule in conjunction with the hardness, shelf stability and security of the solid formulation. The composition of the present invention may be prepared and used as a direct tableting granulation as well as the filler or core for the capsule product. A method and corresponding apparatus are likewise disclosed and contemplated herein.

17 Claims, No Drawings

PROCESS FOR PREPARING SOLID ENCAPSULATED MEDICAMENT

BACKGROUND OF THE INVENTION

The present invention relates generally to encapsulated products containing edible active ingredients such as medicaments, foods and the like, and more particularly, to encapsulated products that offer improved security in combination with extended shelf line and physical integrity.

The products with which the present invention is concerned comprise encapsulated ingestible materials, that have been in broad use and distribution for many years. Such encapsulated products have been prepared by the placement of flowable materials whether in powder or liquid form within the capsule structure which is generally prepared as two telescoping capsule halves. Accordingly, the contents of the encapsulated product are located within the capsule halves, and the capsule halves are then brought together into telescopic engagement and are thereafter sealed, whereupon the contents of the capsule are secured. Generally, such capsules are employed on the pharmaceutical and food industries and hold various edible and pharmaceutically active materials, such as medicines, vitamin preparations and the like. The materials from which the capsule halves are prepared are usually hydrophilic, and are thereby adapted to dissolve in the intestines after ingestion.

One of the prevalent difficulties and drawbacks to the use of capsules in the manner stated above has been their tendency to disengage and to prematurely release their contents. Accordingly, the prior art contains numerous disclosures directed to the establishment and maintenance of a sealing engagement between the capsule halves.

The problem of this engagement became more acute during the early part of this decade with the advent of the deliberate disengagement of encapsulated medicaments and the placement therein of certain poisons. Such deliberate activity was possible because of the inadequate sealing engagement between the capsule halves, and resulted in the decision by several of the major pharmaceutical firms to abandon the use of capsules as a dosage form for their medicaments. As a result, the pharmaceutical industry moved toward the use of a solid dosage form which externally resembled the capsule and which was known as the caplet. This dosage form, however, has met with limited consumer acceptance, and as a result, the manufacturers have now attempted to remedy this situation by the placement of a coating or capsule about the solid caplet, in an effort to improve the organoleptic properties of the dosage form.

A variety of techniques are therefore in use for the preparation of this composite solid dosage form, including the initial preparation of the caplet followed by the dipping, spraying or other application of an outer coating such as gelatin, and the friction-fit application of hollow capsules to the rigid caplets. Both of these approaches are time-intensive and frequently result in a product that is inadequate both commercially and for security reasons. The ability of the capsule halves to be dislodged from each other remains with the result that one can tamper with this solid dosage form and dispose a poison interstitially between the capsule half and its contents.

In addition to the shortcomings of the processes in use presently, Applicants have reviewed other literature relating to this subject and find no disclosures in the prior art respecting the products and corresponding processes of the present invention. For example, U.S. Pat. No. 3,432,592 to Speiser discloses the injection molding of an oral medicament in solid form, utilizing thermoplastic synthetic resins that are either insoluble or are of limited solubility, in large quantities for the purpose of developing delayed-release formulations. The resins used by Speiser include both polycondensation and polyaddition resins which are present in amounts of from 60% to 80% of the total tablet content. The temperature at which these materials are processed is substantially elevated and, for example, ranges upwards of 80° C. to 160° C. Such formulations, however, because of their limited solubility and composition are only useful in the instance where delay in release of the active ingredient is desired. Moreover, the elevated temperature at which the materials are processed would result in an undue amount of loss or attenuation of the active ingredients most commonly formulated by encapsulation, as the ingredients would either break down or would flash off at these temperatures. Accordingly, the disclosure of Speiser does not offer a solution to the problems faced in the capsule art as to the development of prompt release encapsulated materials offering desired organoleptic properties.

U.S. Pat. No. 4,028,024 to Moreland represents an alternative to conventional encapsulation wherein the contents of the capsule and the capsule material are co-extruded and then formed into capsule shapes. The Moreland disclosure relates primarily to the formation of encapsulated product by the simultaneous disposition of the contents of the capsule and the capsule-forming materials in a continuous cylindrical mass which is then individually, cut and shaped to form the encapsulated product. Nothing in Moreland discloses the use of conventional preformed capsules or the preparation of a solid product including solidified capsule contents.

The remaining prior art comprising U.S. Pat. Nos. 4,673,438; 4,591,475; and 4,655,840 all relate to the manufacture of the capsule halves by injection molding techniques, including reference to appropriate capsule-forming compositions. Nothing in these disclosures relates to the formation of solid encapsulated dosage forms and therefore offers no suggestion to the artisan with respect to the problems faced and to appropriate solutions.

The need therefore exists for the development of a solid encapsulated dosage form offering the desired organoleptic properties of an encapsulated product in combination with the security and shelf stability afforded by a solid dosage form.

SUMMARY OF THE INVENTION

In accordance with the present invention, a solid encapsulated product for the per oral delivery of medicaments and other edible agents is disclosed which comprises a capsule shell and a composition adherently disposed therein in solid form, the solid composition comprising an active ingredient selected from the group consisting of pharmaceutical compounds, vitamins, food ingredients and comestibles, and a matrix material present in an amount of up to about 35% by weight of the said solid composition and having a melting point of up to about 100° C. The solid composition is initially prepared as a direct flowable mixture of the active ingredient and the matrix material. The matrix material is then heated to its melting point to cause it to liquify, and the liquified mixture is then introduced into an extrusion or injection molding unit which is associated with conventional capsule filling apparatus in place of the hopper that is presently used for the dispensing of flowable granular capsule contents. Alternatively, the flowable mixture is heated above the melting point of the matrix in the extruder and filled into the capsules.

Accordingly, the present invention further includes a method for the preparation of a solid encapsulated product comprising preparing the flowable mixture of the active ingredient with the ingestible matrix material, heating the mixture to a temperature sufficient to liquify the matrix, introducing the heated mixture into an ingestible hollow capsule in an amount sufficient to substantially completely fill the interior thereof, sealing the capsule thus filled and solidifying the mixture in the sealed capsule to form the solid encapsulated product. As indicated earlier, the heated mixture may be introduced into the hollow capsule by extrusion or injection molding. Thus, for example, the liquified mixture may be introduced into a conventional capsule half that resides within a mold having a cylindrical extension removably disposed thereon to permit the introduction of the additional quantity of composition necessary to fill the mating capsule half thereafter telescopically placed thereover.

After the capsules are filled, the compositions may be solidified by cooling to room temperature, whereupon the matrix material would harden.

As indicated earlier, the matrix materials suitable for the present invention are edible materials having a melting point ranging up to about 100° C. and preferably, from about 60° C. to about 100° C. Suitable matrix materials include carbohydrates such as sorbitol and mannitol, polyalkylene glycols such as the carbowaxes, polyoxyalkylene glycols and mixtures thereof. More particularly, sugar alcohols such as mannitol and sorbitol, gelatin, mannose, and polyethylene glycols having an average molecular weight ranging from about 6,000 to about 10,000.

In a particular embodiment, a mixture of gelatin and a polyethylene glycol having a molecular weight in the aforestated range may be used to achieve a combination of solidification and adherence to the outer capsule, particularly in the instance where the outer capsule is prepared from gelatin. Further, gelatin alone containing 20% water can be used as the matrix and will achieve a combination of solidification and adherence to the outer capsule, particularly in the instance where the capsule is prepared from gelatin.

In a preferred embodiment, the matrix material is present in an amount by weight of the composition ranging from about 5% to about 20%, and more preferably, from about 15% to about 20%.

A further aspect of the present invention is the improvement in security that is gained by the use of the melt formation of the encapsulated solid dosage form. The products thus prepared are tamper evident as the capsules can only be dislodged by heat and will irreversibly deform. Added security through improved bonding of the capsule to its contents can be achieved by preliminarily wetting the interior surface of the capsule with a gelatin solution, water or methanol, and applying to the wetted surface an amount of granular gelatin sufficient to form a roughened wall surface. For example, the wetted surface could be given a dusting of the gelatin granulate that would promptly adhere thereto. The roughened surface would become embedded in the solidified composition thereafter introduced therein, and would offer further resistance to removal of the capsule from the solid core.

The present invention likewise extends to suitable apparatus for the practice of the present method comprising a capsule filling machine including die plates holding the hollow capsule halves and capsule content delivery means, wherein the capsule content delivery means are modified by the replacement of the conventional hopper for flowable granular material, with either an extruder or an injection molding unit with suitable heating means. Likewise, the apparatus of the present invention could be provided with a special die having a multiplicity of die orifices corresponding in number and disposition to the conventional circular capsule half template, whereupon the capsule contents could be simultaneously injected into all of the capsules disposed on the capsule plate. Alternately, the die could provide for a plurality of exit ports disposed in linear relationship either as a single row or in a plurality of rows permitting the indexing and rotation of the plate retaining the capsule halves past the injector or extruder port, whereupon a plurality of capsule halves would be simultaneously filled. The extruder or injector die orifices could define the cylindrical extensions or sprues that would permit the injection or extrusion of the additional capsule composition as discussed earlier, that would upon solidification permit the placement thereover of the mating capsule half.

After assembly, the capsule contents could be dried and sealed by the application of mild heat energy such as by electromagnetic radiation, whereupon the capsule halves would be welded to each other and the matrix material would likewise bond to the interior of the capsule walls.

The capsule products prepared in accordance with the present invention offer several advantages over capsule products presently commercially available. Particularly, the present capsule products offer the security and tamper resistance and evidence available only with solid dosage forms, in combination with the texture and other sensory attributes available only with the use of encapsulated dosage forms. The encapsulated products are likewise advantageous in that they offer improved shelf stability and durability by virtue of the solidification of the capsule contents. The manufacture of the present encapsulated product is simpler and more economical than prior art processes for the preparation of acceptable solid dosage forms and is likewise more rapid.

Accordingly, it is a principal object of the present invention is to provide a solid encapsulated dosage form for an edible ingredient or medicament which is capable of utilizing conventional capsule technology.

It is a further object of the present invention to provide a solid encapsulated product as aforesaid that offers a combination of tamper evidence and improved sensory attributes.

It is a still further object of the present invention to provide encapsulated solid dosage form as aforesaid that is economical and may be rapidly prepared.

It is a still further object of the present invention to provide a method for the manufacture of an encapsulated solid dosage form which is simple and rapid to practice.

It is a still further object of the present invention to provide an apparatus for the practice of the method of the present invention that is capable of rapid and economical operation.

Other objects and advantages will become to those skilled in the art from review of the ensuing detailed description.

DETAILED DESCRIPTION

In accordance with the present invention, an encapsulated solid product for the dosage delivery of an edible active ingredient such as a medicament, food, confection or the like comprises a hollow ingestible capsule shell containing a solidified composition disposed adherently therein, which composition comprises the active ingredient selected from the group consisting of pharmaceutical compounds, vitamins, food ingredients and comestibles, and a matrix material which is present in an amount of up to about 35% by weight of the composition and has a melting point of up to about 100° C. More particularly, the matrix material is present in an amount ranging from about 5% to about 35% by weight, and is preferably present in an amount of from about 10% to about 20%. The matrix material has a melting point ranging from about 60° C. to about 100° C. The matrix material serves to solidify the composition and to thereby render it resistant to tampering and premature disintegration.

The product and associated method of the present invention are based upon a procedure of direct melt formation. Accordingly, the solid composition comprising the active ingredient(s) and the matrix is formed by the melting of the matrix in direct contact with the active ingredient(s) and the consequent coating of the latter by the melted matrix material, and not by the formation of a solution of the matrix which is then combined with the active ingredients. The present procedure is advantageous as it reduces the components that must be included during the preparation of the composition, as well as the number and complexity of the processing steps that are involved. For example, the absence of solvents eliminates the need for solvent evaporation nd drying of the composition and the concomitant exposure of the composition to temperatures that may adversely affect the stability of the active ingredient(s).

A further aspect of the invention is the use of extrusion or injection to promote a mixing of the ingredients as well as to provide an economical and effective method for the filling of the capsules in the formation of the final encapsulated product. The result of both of the distinguishing aspects of the present invention is that the composition as prepared may be easily formed either into a solid dosage form directly from the melt stage such as by the filling of capsule which are thereafter merely cooled to solid state, or may be milled into a dry powder which can then be directly compressed into a solid dosage form.

Suitable matrix materials are edible and hydrophilic, and include carbohydrates, polyalkylene glycols, polyoxyalkylene glycols, and mixtures thereof. More particularly, the matrix material may be selected from polyethylene glycols, polyoxyalklyene glycols, sugars, sugar alcohols, gelatin and mixtures thereof. Accordingly, suitable matrix materials include sugars such as mannose, glucose, galactose, fructose, arabinose, xylose, sucrose, maltose and others. Suitable sugar alcohols include erythritol, arabitol, xylitol, adonitol, mannitol, dulcitol, sorbitol and mixtures.

The matrix may also be prepared from various polyethylene glycols known by a variety of trade names such as Carbowax, PEG, Pluricol E, Poly-G, Polyglycol E and the like. These compounds all have the general formula $H(OCH_2)CH_2)_nOH$, where n is greater than 4. These compounds have previously been used as water soluble lubricants for molds and fibers and in metal-forming operations as well as in food and food packaging. The polyethylene glycols useful in accordance with the present invention have an average molecular weight ranging from about 6,000 to about 10,000 and an average n value exceeding 158. The preferred polyethylene glycol of the present invention is known as Carbowax 8000, which is known to have a melting point of from 60° C. to 63° C. This melting temperature is particularly significant, as it is below the temperature of most of the medicaments and other active ingredients that are encapsulated in accordance with the present invention. This lower temperature thereby assures that the composition of the present invention may be prepared and liquified to the extent necessary to introduce the same into the gelatin capsule without reaching a temperature that would be deleterious to the stability, efficacy or toxicity of the active ingredient to be included in the solid dosage form.

More particularly, the matrix material of the present invention may comprise sugars such as mannose, sugar alcohol such as mannitol and sorbitol, and the polyethylene glycol known as Carbowax 8000. Further, the polyalkylene glycol such as the polyoxyethylene glycols or polyethylene glycol ethers are also useful herein.

While the matrix may melt at temperatures of as high as 100° C., the temperature used in the instance where the melt is introduced into a gelatin capsule should not cause the capsule to exceed its softening temperature during and after the capsule is filled, as this would cause undesirable deformation and distortion of the capsule wall. Such distortion if evident on a previously completed product would reveal tampering, as the contents of the present encapsulated product cannot otherwise be accessed except by heating and removal of the capsule shell. This temperature sensitivity resulting from the adhesive bond between the capsule and its contents provides a further security feature hereof.

The melting or softening temperature of the matrix material may be controlled by the addition of impurities or other melt temperature modulating agents. Such agents should be edible and may be water soluble. For example, the melting temperature of sorbitol may be depressed by the addition of a quantity of glucose, such as set forth in tabular form below.

| SOFTENING TEMPERATURES OF SORBITOL-GLUCOSE BLENDS | | |
|---|---|---|
| GLUCOSE (%) | SORBITOL (%) | SOFTENING TEMP. (°C.) |
| 2% | 98% | 75° C. |
| 4% | 96% | 74° C. |
| 6% | 94% | 72° C. |
| 10% | 90% | 68° C. |
| 15% | 85% | 66° C. |
| 20% | 80% | 61° C. |

Other materials useful as melt temperature modulators may include for example, glycerine, lower molecular weight polyethylene glycols, and the like, it being understood that the modulator like the matrix material, must be edible and preferably water soluble.

In addition to the active ingredient and the matrix material, the composition of the present invention may include other conventional ingredients such as excipients, disintegrants, binders and extenders. Accordingly, ingredients such as cellulose ethers and esters, calcium carbonate, talcum powder, bentonite, alumina, magnesium silicate, magnesium stearate, corn starch, sodium lauryl sulfate, and the like, are contemplated. Particular disintegrants useful in accordance with the present invention are corn starch and a material known as Ac-Di-Sol. The disintegrants may be included in amounts of up to about 20% by weight depending upon the nature of the matrix material and the speed of disintegration that is desired.

In addition to utilizing the composition of the present invention for the preparation of the encapsulated products as defined herein, the composition may also be used for direct compression tableting. In such instance, lubricants such as sodium lauryl sulfate and the like would be added, unless polyethylene glycol is used which is itself a lubricant.

The method of the present invention comprises the preparation of the mixture of the active ingredient in the composition including the matrix material and other standard additives, and the heating of the resulting mixture to a temperature sufficient to liquify the matrix material but inadequate to damage the active ingredient by causing the flashing off or breakdown of the same. Typically, the mixture may be heated to a temperature ranging from about 60° C. to about 70° C., whereupon the matrix material will liquify, and the resulting composition is then in condition for introduction into the hollow capsule.

Accordingly, after heating of the mixture, the same may be introduced into the hollow capsule as by extrusion or injection molding. As indicated earlier, a conventional extrusion or injection unit may be utilized in conjunction with a standard capsule filling machine in place of the conventional hopper that dispenses the flowable granular material that is usually introduced into the capsule halves. The injection molding or extrusion apparatus may be modified to provide a plurality of orifices or dies to facilitate the simultaneous introduction of the liquified composition into a plurality of capsules. Also as noted earlier, a provision for an extension of the chambers holding the individual capsules may be provided either by the extension of the dies on the extruder or injector, or by the disposition of an intermediate plate with appropriate cylindrical openings therein adapted to register with the chambers holding the capsule halves, whereupon an additional amount of the liquid composition may be injected or extruded into the capsule. In this fashion, the excess of the composition would be provided so that upon the placement of the mating capsule half telescopically over the filled capsule, the amount of composition provided is sufficient to assure complete occupancy of the full volume of the resulting assembled capsule product. Naturally, filling of the capsule base with the flowable composition may prove sufficient without overfilling, and the foregoing modification is accordingly optional.

After the filling of the capsule base, the capsule cap may then be introduced thereover to telescopically receive the former, whereupon the completely filled and assembled capsule product may be ejected and transferred for drying and solidification of the capsule contents. Drying may be effected by room temperature cooling, or by the application of further reduced temperature. After solidification, the capsules may be subjected to the further processing wherein the capsule contents may be permanently bonded to the interior of the capsule walls, as by the application of electromagnetic wave energy radiation. In the instance where the matrix includes a quantity of gelatin, adherence of the capsule contents to the capsule walls is enhanced.

As mentioned earlier, the present invention includes an apparatus for the practice of the present method comprising a standard capsule filling machine which has been modified by the inclusion therewith of an extruder or injection molder in place of the conventional hopper utilized for the dispensing of the flowable capsule contents. Thus, the apparatus would include a plurality of container-dispenser means holding, respectively, quantities of capsule bases and capsule caps, movable support means for holding a plurality of said capsule bases and said respective capsule halves, and dispenser means for containing and dispensing a quantity of the capsule contents into the support means for said capsule bases to fill said capsules. Such capsule content dispenser means would comprise in the present instance the extruder or injection molding unit to dispense the composition with the liquified matrix material therein. Optionally and as indicated earlier, the apparatus could include a further die or mold providing an extended surface against which additional of said composition might be injected or extruded, to assure the complete filling of the capsule when the capsule cap is introduced over the capsule base.

The apparatus contemplated in accordance with the present invention would be able to operate at the same speed as conventional capsule filling apparatus, thereby offering comparable economy and speed of manufacture in conjunction with an improved encapsulated product. Moreover, the contemplated apparatus facilitates the development of higher speed encapsulating equipment.

Accordingly, the apparatus of the present invention may comprise a modification of known capsule filling machines made by companies such as Elanco, Roto-Fils, Fratelli Zanosi and other comparable known apparatus. In each instance, the hopper provided for the dispensing of the flowable granular material conventionally contained in capsules is replaced with either an extrusion unit or an injection molding unit adapted to communicate with the plate holding the empty capsule bases, so that the appropriate quantity of flowable composition is dispensed directly therein. Naturally, the foregoing discussion is presented by way of example only as modifications to the apparatus contemplated in accordance with the present invention may be made within the scope hereof.

The present invention will be further illustrated by reference to the following illustrative examples wherein all percentages, unless otherwise specified, are to be considered as percentages by weight.

EXAMPLE 1

In this initial experiment, the feasibility of the present method was explored and confirmed. Accordingly, 100 grams of a dense grade of acetaminophen (hereinafter APAP) and 15 grams of Carbowax 8000 were weighed out and placed in a beaker, and then subjected to heating to a temperature above 60° C., whereupon the mass became dense with the melted Carbowax. The material was then placed in empty size No. 1 maroon capsule bodies, and the damp mass was pressed into the capsules, after which caps were placed over the filled capsule bases and fully applied into the closed position. Ten capsules were prepared in this fashion and then set aside to cool at room temperature.

The completed capsules were weighed and their weights compared in relation to empty capsules. The empty capsules were noted to have a weight of 75 mg. per capsule, whereas the weighted capsules had weights of 684, 666, 675, 660, 658, 680, 672, 675, 662 and 681 mg., respectively. The average weight of the filled capsule was thereby determined to be approximately 671.3 mg., so that the content was determined thereby to be 596.3 mg.

The cooled capsules were then inspected and were found to be desirably hard. The capsules were subjected to disintegration and disintegrated within 12 minutes. Certain of the capsules were further exposed to bonding by placement in a microwave held at ¾ power for 50 seconds. The resulting bond was good. A comparison of the properties of the bonded and unbonded capsules was then made, whereupon it was attempted to remove the capsule cap from the capsule body. This was possible in the case of the unbonded capsule, although the contents of the capsule could not be removed from the remaining capsule half. In the instance where the capsules were subjected to bonding, the capsule halves could not be separated.

EXAMPLE 2

Further formulations were prepared seeking to determine the operability of varying quantities of the matrix material. Accordingly, four formulations were weighed out as set forth in Table 1 below.

TABLE 1

| INGREDIENTS | FORMULATION (in grams) | | | |
|---|---|---|---|---|
| | 1 | 2 | 3 | 4 |
| APAP-Dense | 100 | 100 | 100 | 100 |
| Carbowax 8000 | 5.26 | 11.11 | 17.6 | 25 |

Formulations 1-4 correspond to matrix contents of 5%, 10%, 15% and 20%, respectively.

The materials were blended and subjected to 60° C. heat until the matrix melted, whereupon equal quantities of the composition were introduced into capsules and filled and sealed as before. All of the capsules thus prepared produced hard cores with the exception of the formulation including 5% of Carbowax 8000 alone, which was of lesser hardness although operable. It was noted that as the percent of matrix increased, the melt was more plastic and easier to manipulate.

EXAMPLE 3

The disintegration of the encapsulated products prepared in accordance with the present invention was examined further by the addition of a disintegrant and the observation as to the effect that such disintegrant had upon disintegration time as well as the other properties of the encapsulated product. Thus, all the capsules were subjected to disintegration, and it was noted that disintegration took place within a maximum of 20 minutes, with the capsules prepared with 5% Carbowax disintegrating within 5 minutes, and the capsules containing 20% of the matrix Carbowax disintegrating within 19 minutes.

The preparation of specimens with 15% matrix and an included quantity of the disintegrant Ac-Di-Sol produced a reduction in the disintegration time. In particular, in the instance where 400 mg. of Ac-Di-Sol was added to 20 grams of a 15% composition blend, the disintegration time dropped from 16 minutes to 12 minutes. In the instance where 800 mg. of Ac-Di-Sol was added to a similar quantity of 15% matrix material, the disintegration time dropped from 16 minutes to 4 minutes. The capsules thus prepared had been inspected prior to conducting the above disintegration tests, and were found to be sufficiently solid and to thereby possess all of the desired properties of encapsulated prepared in accordance with the present invention.

EXAMPLE 4

Further studies of disintegration including a disintegrant were carried out, and in this instance, 100 grams of APAP, 15 grams of Carbowax 8000, and 2.3 grams of Ac-Di-Sol were blended. The APAP and Carbowax were first blended and melted and thereafter reblended, after which the Ac-Di-Sol was added and further blending took place. Equal quantities of the resulting mixture were placed in six size No. 1 capsules, weighed and tested for disintegration. All capsules were noted to contain over 588 mg. of material of which 500 mg. constituted APAP. Disintegration of the capsules thus prepared was approximately 5 minutes 32 seconds, and it was thereby determined that a size No. 1 capsule could be successfully filled with 500 mg. of APAP as a solid core utilizing a composition having the following ratio of ingredients with respect to each other: Ratio of APAP to Carbowax 8000 to Ac-Di-Sol =100:15:2.3.

EXAMPLE 5

In this experiment, an Elancofil U-90 capsule filling machine was modified for the purpose of filling the capsules in accordance with the present invention. Accordingly, the hopper for use with the flowable granular material was modified for this preliminary test by the inclusion of downwardly directed paddles attached to the shaft of the augur disposed therein, and 150 watt heat lamps were disposed adjacent the hopper to heat the hopper and augur to a temperature of above 60° C. The capsule base supports or rings were preheated in an oven to 70° C. to facilitate the continued heating of the composition after placement in the capsule halves. This procedure was followed as it was felt that the preliminary heating of the hopper and augur might be insufficient to achieve the desired full melting of the matrix material. Naturally, the use of either an extrusion or injection molding unit in place of the heated hopper would obviate the need for the independent heating of the rings.

Capsules were then filled and were found with this preliminary apparatus to result in the formation of solid encapsulated units of favorable weight content and disintegration time.

EXAMPLE 6

The composition of the present invention was formulated and tested for use as a direct compression formulation, i.e., a formulation which is directly used in the manufacture of tablet dosage units. Accordingly, test tablets were prepared having 5%, 10%, 15% and 20%, respectively of Carbowax 8000 and APAP Stock No. C0004. The respective formulations were then prepared into tablets on a Code 10-10 tablet press. The resulting tablets were all excellent.

EXAMPLE 7

Filled capsules containing the composition of the present invention were prepared wherein the APAP component is selected from capsule grade rather than dense material. Accordingly, 1 kg. of capsule grade APAP (Stock No. C0309) and 150 grams of Carbowax 8000 were weighed out and blended on a Hobart blender. The material was then placed in an oven set at 60° C. for two hours. Thereafter, the material was re-blended on a Hobart blender and returned to the oven for 20 minutes at the same temperature. After this second heating, the material was test filled into ten capsules, and it was determined that it was possible to fill the capsules to contain 590 mg. of ingredients (665 mg. of total weight of the encapsulated products). This experiment therefore confirmed that capsule grade APAP was usable and that acceptable solid encapsulated products could be prepared therefrom.

EXAMPLE 8

In this experiment, the ability of a composition in accordance with the present invention to form tablets was further tested. Accordingly, 5 kg. of capsule grade APAP was blended with 250 grams of Carbowax 8000 on a production Triumph blender. The resulting mixture was placed in three containers and held for three hours to melt the Carbowax 8000. Thereafter, each of the quantities of mixture were re-blended, heated and placed in trays to solidify.

After solidification was complete, the material was pressed through a 30 mesh screen to form a granulation. The granulation was then placed in a hopper, and its weight was adjusted to 580 mg. Tablets were thereafter formed and were found to be acceptable in hardness and disintegration.

EXAMPLE 9

Further blends of direct compression formulations were prepared as follows:

TABLE 2

| INGREDIENTS | FORMULATION (in grams) | |
|---|---|---|
| | A | B |
| Dense-APAP | 500 | 500 |
| Carbowax 8000 | 52.6 | 55.6 |

Formulation A reflected a 5% matrix content, while formulation B represented a 10% matrix content.

The materials as above formulated were each blended in a laboratory scale Hobart mixer, after which they were subjected to melting temperatures of 60° C. and spread on an aluminum tray, cooled to harden, and then pressed through a 30 mesh screen. The resulting granular material was then tableted on a rotopress. The material formed tablets easily, then yielded acceptable hardness of 6+ kg. (in elongated tablet) and disintegrated within 8 minutes 15 seconds for the 5% blend and 5 minutes 10 seconds for the 10% blend.

The same formulations indicated above were prepared with 2% Ac-Di-Sol and were then tableted on a layer press. The resulting tablets were excellent in hardness and other properties, and disintegrated in less than one minute.

Further formulations for tableting containing 5%, 10%, 15% and 20% matrix material were prepared as above, including 20% by weight of caffeine, each of the granulations, blending the same and the test tableting. The 5% blend did not produce good tablets, while the 10% blend produced acceptable tablets and the 15% and 20% blend produced good tablets with the 20% blend being the best. Disintegration of these products was slow but was under 30 minutes. It was theorized that a granulation containing 30% Carbowax and APAP would accommodate a higher level of a contaminant such as caffeine in a bulk granulation of this kind.

Moreover, the experiments regarding tableting illustrated that a broad range of matrix concentrations for direct tableting was possible, depending upon the remainder of the material in the composition.

EXAMPLE 10

A further tableting blend containing a material known as CONPAP, Ac-Di-Sol, sodium lauryl sulfate and lactose was prepared for direct tableting at a level of 600 mg. per unit using a capsule shaped punch and die. The tablets thus formed were excellent, disintegrated in less than 2 minutes. Thereafter, the same composition was prepared as a core for a size No. 1 capsule. The cylindrical tablets after formation were then forced into capsules, capped and sealed in a microwave oven at full power for 45 seconds, using methanol as a sealing or dialectic fluid. The resulting product was superior to commercially available products formed by similar procedures but had superior outer appearance.

EXAMPLE 11

Further compositions were prepared in accordance with the present invention to evaluate alternative matrix materials. Accordingly, sorbitol and mannitol were prepared in separate mixtures in the following fashion.

TABLE 3

| INGREDIENTS | FORMULATION (in grams) | |
|---|---|---|
| | C | D |
| APAP-Dense | 100 | 100 |
| Sorbitol | 17.6 | |
| Mannitol | | 17.6 |

The above compositions were then blended and heated until the respective matrix materials melted. The materials were then blended again, and each was pressed into size No. 1 capsules and weighed. The respective capsules when filled weighed 650 mg. in each instance, indicating that 575 mg. of weight were attributable to the ingredients. The products were then cooled and were found to be hard, with sorbitol, however, offering greater resistance to pulverization under pressure. It was therefore determined that higher quantities of both sorbitol and mannitol in the mixture would improve hardness of these capsule cores.

The materials prepared above were prepared as granulations which were then spread on trays, cooled, passed through a 30 mesh screen and then tableted on a layer press. The resulting tablets were desirably hard and possessed the remainder of the favorable properties hereof.

EXAMPLE 12

In this example, a gelatin powder was prepared containing 20% water. This material was then blended with APAP dense, at a ratio of 15 parts gelatin powder to 100 parts APAP. The powder and the APAP were blended, then heated to 95° C. and mulled in a mortar to replicate the action of the extruder, and the resulting mass was then pressed into a capsule and cooled. The resulting capsule contained 500 mg. of APAP and became solid upon cooling. The capsule bonded well to the solid core. Deformation of the capsule at this high temperature was prevented by placing the capsule in an aluminum ring which acted as a heat sink as the capsule was filled.

EXAMPLE 13

A further preparation including a medicament was made wherein 90% acetaminophen, 10% corn starch (Mallincrodt), sodium lauryl sulfate was prepared with Carbowax 8000 and then used to prepare encapsulated products. The resulting products exhibited favorable properties of hardness and adhesion to the capsule in conjunction with effective delivery and full strength and utility of the active ingredient.

While the present disclosure has proceeded with reference to particular matrix materials such as those listed earlier, it is to be understood that other matrix materials are likewise usable. For example, suitable matrix materials also contemplated in accordance with the present invention comprise polymerizable materials that thermoset for time release and thereafter dissolve in body fluid or enzymes. These materials may be used in conjunction with the matrix materials listed above to achieve variations in the time of release of the active ingredient.

This invention may be embodied in other forms or carried out in other ways without departing from the spirit or essential characteristics thereof. The present disclosure is therefore to be considered as in all respects illustrative and not restrictive, the scope of the invention being indicated by the appended claims, and all changes which come within the meaning and range of equivalency are intended to be embraced therein.

What is claimed is:

1. A method for preparing a solid encapsulated product capable of per oral delivery of a medicament or other edible active ingredient without delay comprising:
   a. preparing a flowable mixture comprising at least one orally administrable medicament in an ingestible matrix material having a melting point ranging up to about 100° C.;
   b. heating the mixture of Step a. to a temperature sufficient to liquify said matrix material;
   c. introducing the mixture of Step b. into an ingestible hollow capsule in an amount sufficient to substantially completely fill the interior thereof;
   d. sealing the capsule of Step c.; and
   e. solidifying the mixture in the sealed capsule of Step d. to form said solid encapsulated product, wherein said mixture and said capsule in said solid encapsulated product are integral with each other, and together cause said solid encapsulated product to be tamper-evident.

2. The method of claim 1 wherein said matrix material is selected from the group consisting of carbohydrates, polyalkylene glycols, polyoxyalkylene glycols, and mixtures thereof.

3. The method of claim 2 wherein said matrix material is selected from the group consisting of polyethylene glycol, polyethylene glycol ether, sugars, sugar alcohols, gelatin and mixtures thereof.

4. The method of claim 3 wherein said matrix material is selected from the group consisting of sorbitol, mannitol, mannose, gelatin,, and polyethylene glycols having a molecular weight in the range of from about 6,000 to about 10,000, polyoxyethylene glycols, and mixtures thereof.

5. The method of claim 1 wherein said matrix material is present in an amount of up to about 35% by weight.

6. The method of claim 5 wherein said matrix material is present in an amount of from about 5% to about 35% by weight.

7. The method of claim 6 wherein said matrix material is present in an amount of from about 10% to about 20% by weight.

8. The method of claim 4 wherein said matrix material comprises a polyethylene glycol having a molecular weight of from about 6000 to about 10,000 in an amount of from about 5% to about 20% by weight.

9. The method of claim 8 wherein said matrix material comprises a mixture of a polyethylene glycol having a molecular weight of from about 6,000 to about 10,000, and gelatin.

10. The method of claim 4 wherein said matrix comprises a mixture of said polyethylene glycol and said gelatin and is present in a total amount of from about 5% to about 20% by weight.

11. The method of claim 4 wherein said matrix comprises sorbitol.

12. The method of claim 4 wherein said matrix comprises mannitol.

13. The method of claim 1 wherein said matrix includes an edible, water soluble melting point modulator.

14. The method of claim 1 wherein Step c. is performed by extrusion.

15. The method of claim 1 wherein Step c. is performed by injection molding.

16. The method of claim 1 wherein the capsule is pretreated before Step c. by wetting the interior surface thereof followed by dusting the wetted interior surface with a quantity of granular gelatin in an amount sufficient to roughen said interior 17. The method of claim 1 further including the step of treating the encapsulated product at Step e. by application of thermal energy to seal the said capsule to itself and to said solid composition.

* * * * *